United States Patent [19]
Mar

[11] Patent Number: 5,330,524
[45] Date of Patent: Jul. 19, 1994

[54] DEFIBRILLATION ELECTRODE WITH MESH CONFIGURATION

[75] Inventor: Craig E. Mar, Fremont, Calif.
[73] Assignee: Ventritex, Inc., Sunnyvale, Calif.
[21] Appl. No.: 79,689
[22] Filed: Jun. 17, 1993

Related U.S. Application Data

[63] Continuation of Ser. No. 759,670, Sep. 13, 1991, abandoned.

[51] Int. Cl.[5] ............................................. A61N 1/36
[52] U.S. Cl. .................................................... 607/129
[58] Field of Search ......................... 607/115, 116, 129

[56] References Cited

U.S. PATENT DOCUMENTS 4,640,983  2/1987  Comte ............................. 128/784
4,827,932  5/1989  Ideker et al. .................... 128/784
5,042,463  8/1991  Lekholm ......................... 128/784
5,044,374  9/1991  Lindemans et al. ............. 128/784

Primary Examiner—William E. Kamm
Assistant Examiner—Scott M. Getzow
Attorney, Agent, or Firm—Steven M. Mitchell; Mark J. Meltzer

[57] ABSTRACT

An implantable cardiac defibrillation electrode is provided, in which there is an electrically conductive wire mesh formed of crossed spirally wound cables. Each of the spirally wound cables comprises a plurality of stranded wire elements, with a central wire element and a plurality of outer wire elements wound adjacent the central wire element. In one embodiment, the crossed cables are formed in a twill weave pattern, alternating over and under at least two individual cables.

4 Claims, 3 Drawing Sheets

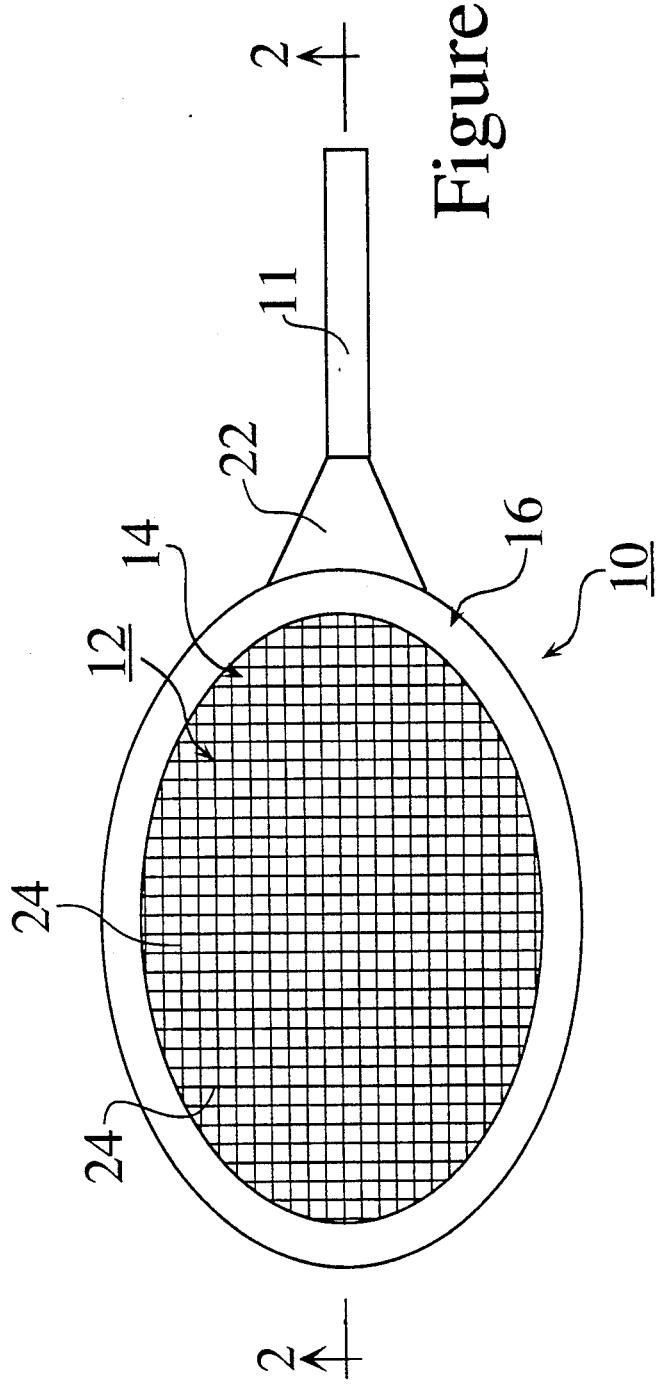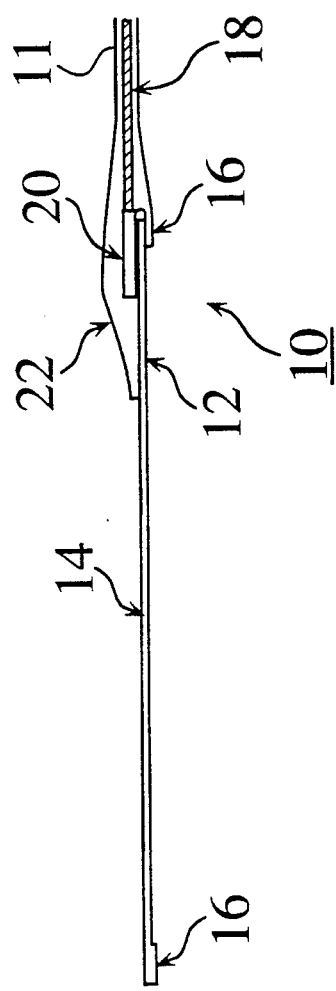

DEFIBRILLATION ELECTRODE WITH MESH CONFIGURATION

This is a continuation of application Ser. No. 07/759,670 filed on Sep. 13, 1991 now abandoned.

FIELD OF THE INVENTION

The present invention relates to medical electrical stimulation electrodes in general and to implantable defibrillation electrodes in particular.

BACKGROUND OF THE INVENTION

It is well known that cardiac arrhythmias may be controlled with devices such as implantable defibrillators. Past approaches to electrodes used with such devices have employed endocardial electrodes as disclosed in Mirowski et al. U.S. Pat. No. 3,942,536 and Kinney et al. U.S. Pat. No. 4,161,952 or epicardial electrodes as disclosed in Heilman et al. U.S. Pat. No. 4,030,509 and Heilman et al. U.S. Pat. No. 4,291,707.

For systems using epicardial electrodes several functional requirements must be met. The electrodes must be able to deliver large amounts of electrical energy. Electrodes that have large surface areas are desirable since energy can be delivered over a larger area of the heart and current is distributed through greater electrode surface area. Thus current densities and the chance of damaging heart tissue is lessened. Past epicardial patch electrodes have used screens or mesh as disclosed in Heilman et al. U.S. Pat. No. 4,030,509, to accomplish this function.

The electrodes must be flexible enough to conform to the heart. Electrodes which are flexible are not only easier to manipulate and surgically implant, they are also more likely to conform to the heart thus ensuring reliable electrical contact with heart tissue.

The electrodes must be fatigue resistant. The environment that the electrode is in must endure constant motion and millions of flex cycles. Prior art patch electrodes have used space wound coils for flexibility and enhanced fatigue life as disclosed in Holleman et al. U.S. Pat. No. 4,971,070.

Other objects and advantages of the present invention will become apparent as the description proceeds.

SUMMARY OF THE INVENTION

In accordance with the present invention, an implantable cardiac defibrillation electrode is provided. The electrode comprises an electrically conductive wire mesh formed of crossed spirally wound cables. Each of the cables comprises a plurality of stranded wire elements.

In the illustrative embodiment, each of the cables comprises a central wire element and a plurality of outer wire elements wound adjacent to the central wire element. The wire elements of each cable are substantially parallel to each other and are twisted along their length to form the spirally wound cable.

In one embodiment, each of the cables comprises a core wire element and outer wire elements, with the core wire element having a larger diameter than the diameter of the outer wire elements.

In one embodiment, each of the cable comprises a core wire element and outer wire elements, with the core wire element being formed of a more fatigue-resistant material than the material from which the outer wire elements are formed.

In one embodiment, the outer wire elements are formed of a more corrosion resistant material than the material from which the core wire element is formed.

In the illustrative embodiment, the electrode includes an insulative backing and the electrode also includes a rim surrounding the mesh.

In the illustrative embodiment, the mesh is generally planar and the crossed cables are formed in a rectilinear weave pattern.

Mesh constructed out of stranded multielement wire has several advantages. The stranded wire mesh is more flexible because it is made of smaller wires, thus it conforms to the heart much better than existing electrodes made with larger diameter wire mesh. The stranded wire mesh also has longer fatigue life when compared to the mesh used in prior art devices. This is because for similar deflections and motions the electrode sees, the stress levels for the smaller stranded wire mesh is greatly lessened. In addition the multielement stranded wire is redundant allowing for continuing functionality even if one element of the strand breaks. Stranded multielement wire mesh has greater reliability than prior art electrode mesh. A multielement strand allows for a larger amount of electrode surface area to be exposed to the heart, thus lowering current densities at the electrode/tissue interface.

The electrode made with the stranded multielement wire mesh could be fabricated into an oval or elliptical shape as shown or in other rectangular, circular or similar geometries.

A more detailed explanation of the invention is provided in the following description and claims, and is illustrated in the accompanying drawings.

BRIEF DESCRIPTION OF THE DRAWINGS

FIG. 1 is a bottom plan view of a defibrillation electrode constructed in accordance with the present invention.

FIG. 2 is a cross section of the defibrillation electrode of FIG. 1, taken along the plane of the line 2—2 of FIG. 1.

DETAILED DESCRIPTION OF THE ILLUSTRATIVE EMBODIMENTS

Figure 3:
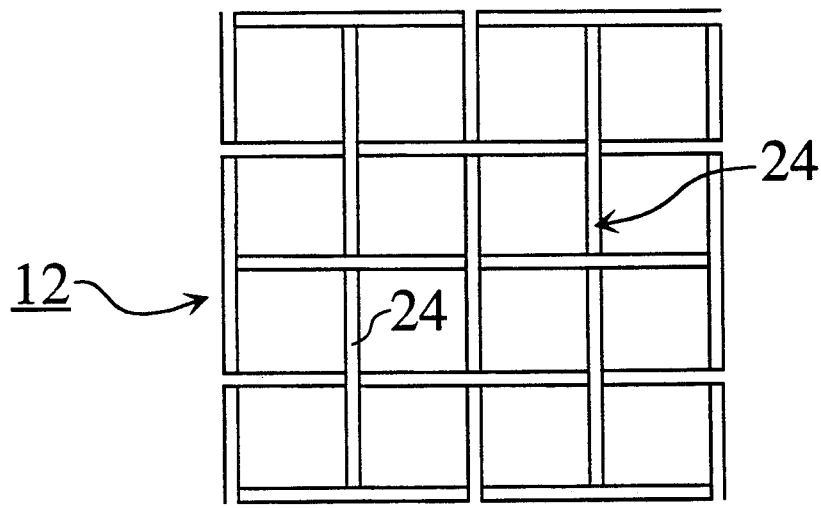
FIG. 3 is a magnified diagrammatic view of the surface of a defibrillation electrode illustrating a standard mesh configuration.

Referring to the figures, FIG. 1 is a bottom plan view of a defibrillation electrode 10 at the distal end of lead 11. The electrode is composed of a generally planar metal mesh 12, a silicone rubber backing 14, and a suture rim 16.

In FIG. 1 the electrode is elliptical in configuration. This allows for a large amount of surface area in a compact, atraumatic shape. The electrode shape could be rectangular, oval, circular or various other shapes.

FIG. 2 is a cross section of the defibrillation electrode. In this view the electrode mesh 12 is connected to an insulated conductor 18 via a connection joint 20. This joint is totally encapsulated in a strain relief 22, typically made of silicone rubber.

As illustrated in FIG. 3, metal mesh 12 is formed of a number of cables 24 woven in a standard mesh. It can be seen that the cables 24 go over and under each other in an alternate manner.

Figure 4:
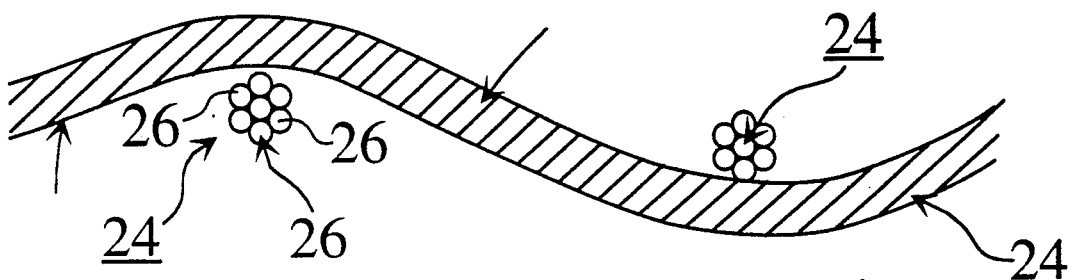
FIG. 4 is a diagrammatic cross section and side view of the stranded wire cable used to fabricate the mesh of the electrode of FIG. 3.

FIG. 4 is a cross section of the cables used to fabricate the metal mesh 12 of the electrode of FIG. 3. Cable 24 is composed of several smaller wire elements 26, which are stranded together. Typically the outer wire elements are wound about a central element, as shown. In the preferred embodiment shown the individual wire diameter is 0.0013 inch and the cable is composed of seven elements. Thus the cable has an overall diameter of 0.004 inch. The elements need not all be the same size, and it may be advantagious to use a larger core wire and smaller outer wires for fatigue or electrical conduction considerations.

It is also possible that the individual wires be composed of different materials. For example, the outer wires could be made with a very corrosion resistant material such as platinum or a platinum alloy and the inner core wire or wires could be made of a fatigue resistant material such as MP35N. Other biocompatible materials such as 316L stainless steel, titanium, carbon, or iridium may be used.

Figure 5:
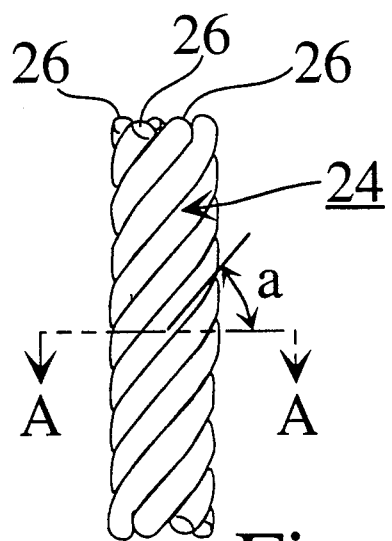
FIG. 5 is a view of a portion of the cable of FIG. 4.

FIG. 4 shows a stranded wire cable 24 composed of seven wire elements 26; however the number of elements could be less or greater depending on the properties desired. It can be seen from FIG. 5 that the wire elements 26 are arranged so that they form a spiral helical three dimensional shape. This spiral shape allows the individual wire strands 26 to flex easier under bending loads since stresses on the wire are lessened. The pitch of the helix of the cable 24, can be varied to allow for different numbers of elements in the strand or to give different flexibilities to the wire strand. In the preferred embodiment shown, the pitch a of the strands 26 (See FIG. 5) is typically about 77 degrees with respect to a plane A—A that is perpendicular to the axis of the cable 24, with about 28 spirals per inch of cable.

Figure 6:
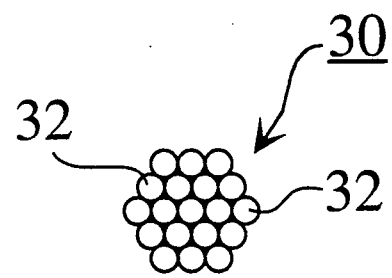
FIG. 6 is a cross section of a 19 element stranded wire cable that could be used to make the mesh.

FIG. 6 is a cross section of an alternate cable 30 that could be used to make the mesh 12. In this configuration, nineteen wire elements 32 are used to make up the cable 30. Changing the number of elements in the strand could give different flexibilities, increased reliability or other desirable properties. The cable could be made of three or more elements.

Figure 7:
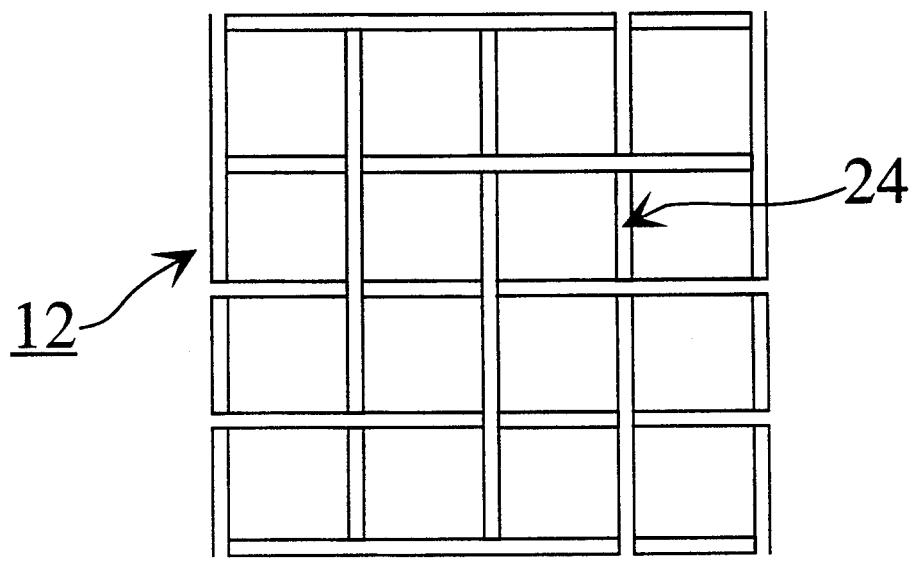
FIG. 7 is a magnified diagrammatic view of the surface of a defibrillation electrode illustrating a twill weave mesh configuration.

FIG. 7 diagrams a magnified plan view of the surface of a defibrillation electrode detailing an alternate mesh configuration. In this diagrammatic view the cables 24 are woven in a twill weave configuration. This configuration is characterized by the weave pattern in which wire strands go over at least two consecutive wire strands and then under at least two consecutive wire strands in an alternate matter.

Figure 8:
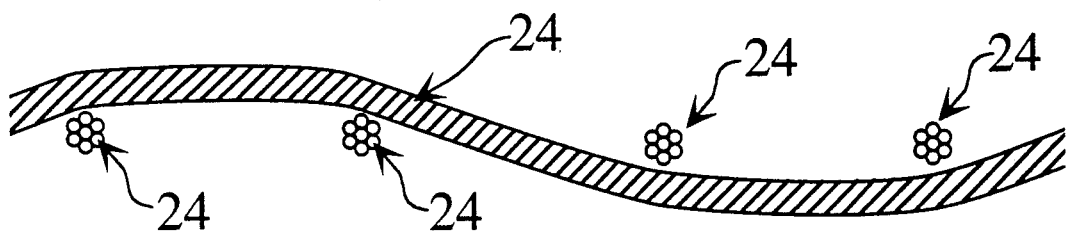
FIG. 8 is a diagrammatic cross section and side view of the twill weave mesh of FIG. 7.

FIG. 8 shows a cross section and side view of the twill weave mesh of FIG. 7. In this view it is easy to see the under two wires/over two wires configuration of the twill weave mesh. It can also be seen that the cables 24 are less bent than cables in the standard weave pattern of FIGS. 3-4. This would allow for less stress induced on the wire during the mesh manufacture as well as less stress during the actual conditions the electrode would be subjected to. Thus, this configuration should allow for increased flex life and reliability.

Although illustrative embodiments of the invention have been shown and described, it is to be understood that various modifications and substitutions may be made by those skilled in the art without departing from the novel spirit and scope of the present invention.

What is claimed is:

1. An implantable cardiac defibrillation electrode which comprises:
    an electrically conductive wire mesh formed of crossed spirally wound cables, each of said cables comprising a plurality of stranded wire elements;
    said crossed cables being formed in a rectilinear twill weave pattern, with each cable going over at least two consecutive cables and then under at least two consecutive cables in an alternate manner.

2. An electrode as defined by claim 1, said electrode including an insulative backing; and a rim surrounding said mesh.

3. An electrode as defined by claim 1, in which said mesh is generally planar.

4. An implantable cardiac defibrillation electrode which comprises:
    an electrically conductive wire mesh comprising a plurality of spirally wound electrical conductors, said mesh being formed in a rectangular twill weave pattern, with each electrical conductor going over at least two consecutive electrical conductors and then under at least two consecutive electrical conductors in an alternate manner.

* * * * *